United States Patent [19]

Patono

[11] Patent Number: 4,769,132
[45] Date of Patent: Sep. 6, 1988

[54] DEVICE FOR CONTROLLING THE WATER BALANCE OF PATIENTS UNDERGOING HAEMODIALYSIS

[75] Inventor: Carlo Patono, Turin, Italy
[73] Assignee: Miren S.r.l., Medolla, Italy
[21] Appl. No.: 868,941
[22] Filed: May 30, 1986
[30] Foreign Application Priority Data
Jun. 7, 1985 [IT] Italy .................... 4923/85[U]
[51] Int. Cl.$^4$ ........................... B01D 13/00
[52] U.S. Cl. .................... 210/86; 210/95; 210/321.65
[58] Field of Search .......... 210/929, 321.3, 646, 210/645, 85, 86, 87, 95, 321.65

[56] References Cited
U.S. PATENT DOCUMENTS
3,979,284 9/1976 Granger et al. .......... 210/321.3 X
4,132,644 1/1979 Kolberg .................... 210/929 X
4,324,663 4/1982 Hirel et al. .............. 210/929 X FOREIGN PATENT DOCUMENTS
2397197 3/1978 France .................... 210/929

*Primary Examiner*—Frank Spear
*Attorney, Agent, or Firm*—Omri M. Behr

[57] ABSTRACT

A device for controlling the water balance of patients undergoing haemodialysis, the device comprising a dialyser, the input of which is connected to a first vessel containing a given quantity of clean dialysing fluid, and the output of which is connected to a second vessel for receiving the contaminated dialysing fluid; the main characteristic of the present invention consisting in the fact that it comprises first weighing means for weighing the first and second vessels and so determining the change in weight of the same during operation.

8 Claims, 1 Drawing Sheet

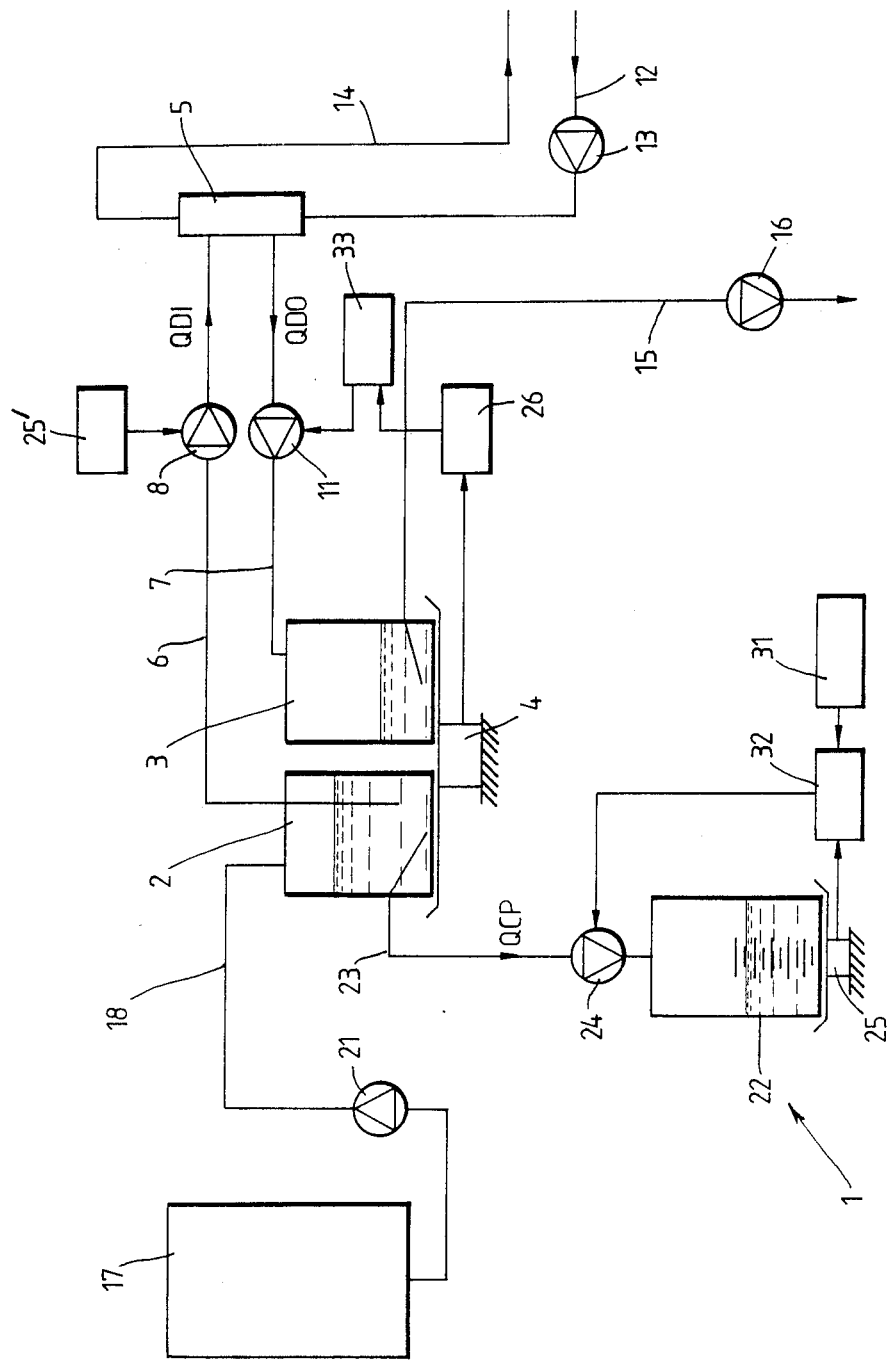

DEVICE FOR CONTROLLING THE WATER BALANCE OF PATIENTS UNDERGOING HAEMODIALYSIS

BACKGROUND OF THE INVENTION

The present invention relates to a device for controlling the water balance of patients undergoing haemodialysis. Haemodialysis treatment is known to consist in feeding the patient's blood into a dialyser having a semipermeable membrane, along a first face of which is fed the patient's blood, and along a second face of which is fed a dialysing fluid. Between the said two membrane faces, substances are exchanged enabling the elimination of metabolic waste and restoration of the electrolytic balance in the blood. During such treatment, steps must also be taken to restore the patient's water balance, by drawing off the water accumulated since the last treatment. To do this, a positive pressure is produced on the blood side of the membrane, and a negative pressure on the dialysing fluid side. The difference between the two pressures, known as transmembrane pressure, causes water to flow, by convection, from the blood into the dialysing fluid.

Successful dialysis treatment depends on accurately controlling the amount of water withdrawn from the blood, falure to do so possibly resulting in the patient manifesting negative and, at times, even critical reactions, such as cardiocirculatory arrest. Furthermore, water withdrawal should be programmed so as to vary appropriately from one patient to another.

Standard dialysers as of present comprise membranes having a relatively low permeability coefficient and, as such, require relatively high transmembrane pressures for withdrawing the required amount of water from the patient's blood. Withdrawal is performed directly by the operator, who checks the weight of the patient lying on a bed fitted with a scale, and adjusts the transmembrane pressure, while at the same time observing the effect of the adjustment on the patient's scale. On such dialysers, transmembrane pressures of around 150-300 mmHg produce no considerable variation in water withdrawal rate, in that, small spontaneous changes in blood pressure, caused, for example, by changes in blood flow, and similar unpredictable changes in the negative pressure of the dialysing fluid, caused, for example, by air bubbles, are both of about 20-30 mmHg/hour. Though the operator may, of course, make the necessary adjustments to transmembrane pressure, by observing the weight of the patient, say, once every half hour or once an hour, drawing off a preset quantity of water per hour is rendered difficult for the reasons already expounded.

Increasing use is currently being made of dialysers comprising membranes with relatively high permeability coefficients, and providing for more efficient and faster cleansing of the blood. Such dialysers, however, have rendered manual control by the operator both difficult and dangerous, by enabling water to be withdrawn at transmembrane pressures of around 20-50 mmHg. As such, normal changes in blood pressure and a rise or fall on the dialyser are sufficient for varying the water withdrawal rate in such a manner as to be intolerable by the patient. An operator must therefore be stationed permanently beside the patient, to prevent sharp changes in the patient's weight from producing the negative reactions already mentioned.

To overcome this drawback, which limits the employment of highly permeable dialysers, control devices are currently used for directly determining the patient's water balance, i.e. the difference between the amount of clean dialysing fluid fed into the dialyser and the amount coming out, which equals the amount fed in plus the amount of water withdrawn from the blood. Currently employed control devices are based on volumetric principles and present two distinct drawbacks. Firstly, volumetric control is affected by the presence of air bubbles, the volume of which depends on the pressure involved. Secondly, the fluid coming out of the dialyser, which is obviously contaminated, is fed into a graduated vessel enabling the operator to assess the amount of fluid withdrawn from the patient. This obviously creates a serious hygiene problem, besides conflicting with strict safety regulations whereby the said contaminated fluid must be fed directly into a drainage network, for preventing anyone from even accidentally coming into contact with it.

SUMMARY OF THE INVENTION

The aim of the present invention is to provide a device for controlling the water balance of patient's undergoing haemodialysis, and which provides for overcoming the aforementioned drawbacks.

With this aim in view, according to the present invention, there is provided a device for controlling the water balance of patients undergoing haemodialysis, said device comprising a dialyser, the input of which is connected, by means of a first duct fitted with a first pump, to a first vessel containing a given quantity of clean dialysing fluid, and the output of which is connected, by means of a second duct fitted with a second pump, to a second vessel designed to receive the contaminated dialysing fluid, said contaminated dialysing fluid being the sum of the said clean dialysing fluid fed into the said dialyser, and the fluid and metabolic waste withdrawn by the said dialyser from the patient's blood; characterised by the fact that it comprises first weighing means for weighing the said first and the said second vessel and so determining the change in weight of the said first and the said second vessel during operation of the said first and the said second pump.

BRIEF DESCRIPTION OF THE DRAWING

A preferred embodiment of the present invention will be described, by way of a non-limiting example, with reference to the attached drawing showing a block diagram of a device for controlling the water balance of patients undergoing haemodialysis, and indicated as a whole by number 1.

DETAILED DESCRIPTION OF THE INVENTION

Device 1 comprises two vessels, 2 and 3, weighing down on a load cell 4 and, in use, containing clean and contaminated dialysis fluid respectively. As described later on, vessel 2 will, of course, be full, and vessel 3 empty at the start of treatment. Device 1 also comprises a dialyser 5 shown schematically in block form in the diagram and having an internal membrane separating two hydraulic circuits, the first relative to circulation of the dialysing fluid, and the second to circulation of a patient's blood. The said first circuit presents a first duct 6 connecting vessel 2 to dialyser 5, and a second duct 7 connecting dialyser 5 to vessel 3. Ducts 6 and 7 are fitted with respective pumps 8 and 11. The said second circuit presents a first duct 12 fitted with a pump 13 and connecting the patient (not shown) to dialyser 5, and a second duct 14 connecting dialyser 5 to the patient. By means of duct 15 fitted with pump 16, vessel 3 is also connected to a drain (not shown).

Number 17 on the attached drawing indicates a clean dialysing fluid tank connected to vessel 2 by means of duct 18 fitted with pump 21. Device 1 also comprises a third graduated vessel 22, connected to vessel 2 by means of duct 23 fitted with pump 24, and weighing down on a load cell 25. Load cells 4 and 25 are transducer devices, i.e. designed to convert the weight exerted on them into a corresponding electric signal.

Pump 8 is fitted with a speed regulator 25' for regulating the flow of clean dialysing fluid along duct 6 as required. Device 1 also comprises an electric member 26 possibly consisting of an amplifier and connected to load cell 4 for detecting, in use, any off-balance of load cell 4, and for controlling pump 11 in such a manner as to regulate fluid flow along duct 6 and so restore the balance on load cell 4. In other words, the said load cell 4 must be subjected at all times to the same weight consisting of the clean dialysing fluid (vessel 2) and the contaminated fluid (vessel 3). Finally, device 1 comprises an electrical member 31 consisting, for example, of an electronic processor, by means of which the operator may programme the flow of clean dialysing fluid along duct 23. Pump 24 is fitted with a flow regulator which forms part of an electronic member 32 connected to member 31 and load cell 25. Member 32 presents an amplifier, for amplifying the signal from load cell 25 and relative to the weight exerted on the same, and a comparator, for comparing the said signal with a signal from member 31 and relative to the programmed weight of the clean dialysing fluid. Depending on the outcome of the said comparison, member 32 controls pump 24 in such a manner as to regulate flow along duct 23 and bring the actual weight exerted on load cell 25 gradually closer to the weight programmed according to even a non-linear function.

As already stated, at the start of treatment, vessel 2 is full, containing a given amount of clean dialysing fluid, whereas vessels 3 and 22 are empty. By adjusting pump 8 by means of speed regulator 25', clean dialysing fluid is withdrawn from vessel 2 and fed into dialyser 5. At the same time, a given amount of clean dialysing fluid is also withdrawn from vessel 2 by means of pump 24. Such double withdrawal reduces the weight exerted on load cell 4, thus activating member 26, which detects the off-balance on load cell 4 and operates pump 11 for restoring the balance of cell 4. As already stated, duct 7 contains a flow of contaminated dialysing fluid from dialyser 5, consisting of the clean dialysing fluid fed into dialyser 5, plus the metabolic waste and accumulated water removed from the patient's blood by the membrane on dialyser 5. During operation of pump 8, the patient's blood is naturally fed along duct 12 by means of pump 13. If QDI indicates the flow of clean dialysing fluid fed into dialyser 5 by pump 8, QDO the flow of contaminated dialysing fluid withdrawn from dialyser 5 by pump 11, and QCP the flow of clean dialysing fluid withdrawn by pump 24 from vessel 2 and fed into vessel 22, water balance is therefore maintained according to the equation:

$$QDI + QCP = QDO$$

or:

$$QCP = QDO - QDI$$

In other words, flow QCP is axactly equal to the difference between the output and input flow from and to dialyser 5, i.e. the amount of fluid withdrawn from the patient by virtue of the transmembrane pressure created by pumps 13 and 11.

As pump 24 is regulated independently of the others, pump 11 providing at all times for reintegrating its flow and so maintaning the balance on load cell 4, water may be withdrawn from the patient linearly, by programming pump 24, by means of member 31, to operate at a given fixed speed, or non-linearly according to a given function also programmed on member 31. Whichever the case, member 32 provides for comparing the flow of dialysing fluid from vessel 2 with that programmed on member 31, and for controlling pump 24 accordingly. Operation of device 1 as described is maintaned until vessel 2 is completely or almost empty. Once vessel 2 has been emptied, vessel 3 is drained off by means of pump 16 and, at the same time, vessel 2 refilled by means of pump 21. At this stage, load cell 4 is obviously subjected to a variable load and no longer in a position to control pump 11 by means of member 26. To overcome this drawback, an electrical member 33, connected to member 26 and pump 11, memorises the speed of pump 11, during normal operating mode, and, while vessel 3 is being drained and vessel 2 refilled, operates pump 11 at a fixed speed equal to the average speed detected over a given preset period, e.g. the last five minutes of normal operating mode. It should be pointed out that the electrical members described herein and shown schematically on the attached drawing are all known, obviously in other spheres, and therefore easily available on the market. All or some of the said members could form part of an electronic processor for controlling pumps 8, 11 and 24 and load cells 4 and 25 on device 1. During the draining stage, pump 13 is kept running, so as to keep the blood circulating and so prevent it from clotting. All the pumps shown schematically on device 1 are obviously fitted with respective motors, not shown for the sake of simplicity.

The advantages of device 1 will be clear from the foregoing description.

In particular, device 1 provides for directly weighing the difference between the fluid fed into and withdrawn from the dialyser, and is therefore unaffected by air bubbles in the fluid. As a rule, the operator is called upon to examine the amount of fluid actually withdrawn from the patient. On device 1, this information is provided by graduated vessel 22, which may be handled safely by virtue of it containing clean dialysing fluid, and therefore conforms with hygiene regulations forbidding any contact with the contaminated fluid. Finally, device 1 enables water withdrawal from the patient to be programmed according to any function programmed on member 31.

To those skilled in the art it will be clear that changes may be made to device 1 as described herein without, however, departing from the scope of the present invention. For example, load cells 4 and 25 may be replaced by other weighing systems, such as electronic or mechanical spring scales or similar. As the weight measured on such scales, however, must be converted into a corresponding electric signal for regulating pumps 11 and 24, provision must also be made for appropriate transducers. The electrical members for regulating pumps 8, 11 and 24 may be other than as described herein. Vessel 22 may be dispensed with on device 1, in which case, the weight reading as measured by load cell 4 provides for determining the weight difference of vessels 2 and 3 and, therefore, the actual amount of fluid withdrawn from the patient. Instead of regulating the speed of pump 11 for maintaining the weight measured by load cell 4 constant, member 33 regulates the speed of pump 11 so that the increase in the weight measured by load cell 4 equals the fall in weight of the patient as required by the operator.

I claim:

1. A device for controlling the water balance of patients undergoing haemodialysis with a control signal, said device comprising: a dialyser, the input of which is connected, by means of a first duct, to a first vessel containing a given quantity of clean dialysing fluid, and the output of which is connected, by means of a second duct, to a second vessel designed to receive the contaminated dialysing fluid, said contaminated dialysing fluid being the sum of said clean dialysing fluid fed into said dialyser, and the fluid and metabolic waste withdrawn by said dialyser from the patient's blood, said device further comprising pump means having a first and second pump and a drive terminal for receiving said control signal, said first pump being fitted to said first duct, said second pump being fitted to said second duct, said first and second pump being driven at a drive ratio varying in response to said control signal on said drive terminal; said device further comprising first weighing means for weighing said first vessel and said second vessel and for producing a weight signal corresponding to the combined weight of said first and second vessel and so determining the change in weight of said first vessel and said second vessel;

first electrical means coupled between said second pump and said first weighing means for keeping weight on the latter constant by regulating the former in response to changes in said weight signal;

a third vessel;

a third pump having a third duct connecting said third pump between said first and third vessel;

second weighing means for weighing said third vessel and for producing a weight signal corresponding to the weight of said third vessel; and second electrical means coupled to said third pump for regulating it.

2. A device as claimed in claim 1, characterised by the fact that said second electrical means comprise:

an electronic processor for programming, according to a given function, the amount of clean dialysing fluid fed along said third duct, and a comparing member for providing a comparison signal in response to the difference between the programmed fluid quantity and the weight of said third vessel, as measured by said second weighing means, and therefore the weight of said quantity of fluid contained in said third vessel.

3. A device as claimed in claim 2, characterised by the fact that the said third vessel (22) is graduated.

4. A device as claimed in claim 2, characterised by the fact that the said first pump (8) is provided with a regulator (25').

5. A device as claimed in claim 1, characterised by the fact that the said second vessel (3) is connected to a drain network by means of a fourth duct (15) fitted with a fourth pump (16).

6. A device as claimed in claim 1, characterised by the fact that the said first (4) and second (25) weighing means comprise respective load cells, i.e. transducers for converting the supported weight into a corresponding electric signal.

7. A device as claimed in claim 1, characterised by the fact that the said first (4) and second (25) weighing means comprise respective mechanical scales connected respectively, by means of transducers, to the said second (26) and first (31, 32) electrical means.

8. A device as claimed in claim 1 characterised by the fact that it comprises a clean dialysing fluid tank (17) connected to said first vessel (2) by means of a feeding duct (18) fitted with a pump (21).

* * * * *